United States Patent
Fang et al.

(12) 
(10) Patent No.: US 6,197,545 B1
(45) Date of Patent: Mar. 6, 2001

(54) GENETICALLY ENGINEERED YEAST WITH MODIFIED SIGNAL PEPTIDASE COMPLEX

(75) Inventors: Hong Fang; Neil Green, both of Chapmansboro; Luc Van Kaer, Nashville, all of TN (US)

(73) Assignee: Vanderbilt University, Nashville, TN (US)

( * ) Notice: Subject to any disclaimer, the term of this patent is extended or adjusted under 35 U.S.C. 154(b) by 0 days.

(21) Appl. No.: 09/269,345

(22) PCT Filed: Sep. 25, 1997

(86) PCT No.: PCT/US97/17597

§ 371 Date: Mar. 25, 1999

§ 102(e) Date: Mar. 25, 1999

Related U.S. Application Data

(60) Provisional application No. 60/026,674, filed on Sep. 25, 1996.

(51) Int. Cl.$^7$ .............................. C12N 15/81; C12N 1/00; C12N 1/19
(52) U.S. Cl. ................ 435/69.1; 435/254.2; 435/254.21; 435/254.22; 435/254.23; 435/471
(58) Field of Search ........................... 435/254.2, 254.21, 435/254.22, 254.23, 471, 69.1

(56) References Cited

U.S. PATENT DOCUMENTS

| | | |
|---|---|---|
| 5,538,863 | 7/1996 | Price . |
| 5,602,034 | 2/1997 | Tekamp-Olson . |
| 5,618,676 | 4/1997 | Hitzeman et al. . |
| 5,631,144 | 5/1997 | Lemoine et al. . |
| 5,854,018 | 12/1998 | Hitzeman et al. . |
| 5,856,123 | 1/1999 | Hitzeman et al. . |

OTHER PUBLICATIONS

Berendsen, Science, vol. 282, pp. 642–643, Oct. 1998.*
Fang et al. "The Homologue of Mammalian SPC12 is Important for Efficient Signal Peptidase Activity in *Saccharomyces cerevisiae*" *J. Biol. Chem.* 271(28):16460–16465, Jul. 12, 1996.

Kalies K. and Hartmann E. "Membrane Topology of the 12– and the 25–kDa Subunits of the Mammalian Signal Peptidase Complex" *J. Biol. Chem.* 271(7):3925–3929, Feb. 16, 1996.

Greenburg G. and Blobel G. "cDNA–derived Primary Structure of the 25–kDa Subunit of Canine Microsomal Signal Peptidase Complex" *J. Biol. Chem.* 269(41):25354–25358, Oct. 14, 1994.

Shelness G. and Blobel G. "Two Subunits of the Canine Signal Peptidase Complex are Homologous to Yeast SEC11 Protein" *J. Biol. Chem.* 265(16):9512–9519, Jun. 5, 1990.

Greenburg et al. "A Subunit of Mammalian Signal Peptidase is Homologous to Yeast SEC11 Protein" *J. Biol. Chem.* 264(27):15762–15765, Sep. 25, 1989.

Shelness et al. "cDNA–derived Primary Structure of the Glycoprotein Component of Canine Microsomal Signal Peptidase Complex" *J. Biol. Chem.* 263(32):17063–17070, Nov. 15, 1988.

* cited by examiner

*Primary Examiner*—Terry McKelvey
(74) *Attorney, Agent, or Firm*—Needle & Rosenberg, P.C.

(57) ABSTRACT

The present invention provides a yeast cell comprising a nucleic acid functionally encoding a eukaryotic (e.g., mammalian) protein homologue of a subunit (Sec11p, Spc1p, Spc2p and/or Spc3p) of the yeast signal peptidase complex. The yeast cell of this invention can be, for example, of the genus Saccharomyces, Schizosaccharomyces, Pichia, Hansenula, Kluyveromyces and/or Yarrowia. Furthermore, the yeast cell can lack one or more functional subunits (Sec11p, Spc1p, Spc2p and/or Spc3p) of the yeast signal peptidase complex. The present invention further provides a method for producing a protein heterologous to a yeast cell comprising expressing, in the yeast cell of this invention, a nucleic acid functionally encoding the heterologous protein under conditions which permit the expression of the nucleic acid as a precursor protein having a signal peptide and processing of the precursor protein to a signal peptide-cleaved form of the protein.

40 Claims, No Drawings ously little is known

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

GTTGATCATC ATCTTAGA                                    18

(2) INFORMATION FOR SEQ ID NO:2:

(i) SEQUENCE CHARACTERISTICS:
      (A) LENGTH: 18 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

CGACGTGCTG TATAATGA                                    18

(2) INFORMATION FOR SEQ ID NO:3:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:3:

CGGGATCCAT GAACAAGCGG CAG                            23

(2) INFORMATION FOR SEQ ID NO:4:

(i) SEQUENCE CHARACTERISTICS:
      (A) LENGTH: 27 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:4:

GGGGAATTCT CTTTTTAGGA TTCACGT                     27

(2) INFORMATION FOR SEQ ID NO:5:

(i) SEQUENCE CHARACTERISTICS:
    (A) LENGTH: 27 base pairs
    (B) TYPE: nucleic acid
    (C) STRANDEDNESS: single
    (D) TOPOLOGY: linear (ii) MOLECULE TYPE: DNA (genomic)

(xi) SEQUENCE DESCRIPTION: SEQ ID NO:5:

GGGGATCCAC GCCAGCCATG CTGGAGC                                27

(2) INFORMATION FOR SEQ ID NO:6:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:6:

GGGGAATTCA ACCCAACTGG GCTAGAAA                               28

(2) INFORMATION FOR SEQ ID NO:7:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:7:

GGGGATCCGG CCGCGCCATG CTGTCTC                                27

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

GGGGAATTCT TACTCACGAT GGACCAG                                27

(2) INFORMATION FOR SEQ ID NO:9:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

GGGGATCCAG CCCGCCATGG TGCGCGCGG                              29

(2) INFORMATION FOR SEQ ID NO:10:

(i) SEQUENCE CHARACTERISTICS:
        (A) LENGTH: 27 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:10:

GGGGAATTCT CTTTTTAGGA TTCACGT                              27

(2) INFORMATION FOR SEQ ID NO:11:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

GGGGATCCAT GAACACGGTG CTGTCG                               26

(2) INFORMATION FOR SEQ ID NO:12:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

GGGATCGATT TAATAACTCT TCGTTA                               26

(2) INFORMATION FOR SEQ ID NO:13:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

GGGGATCCAC AGACAAGATG GCGGCGGCGT CT                        32

(2) INFORMATION FOR SEQ ID NO:14:

(i) SEQUENCE CHARACTERISTICS:
        (A) LENGTH: 32 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:14:

GGGGAATTCT ACTTTATCCA TTTTAAGTTC TG                        32

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

```
        (xi) SEQUENCE DESCRIPTION: SEQ ID NO:15:

CGGGATCCAC ACGTGAATAC TACC                                                24

(2) INFORMATION FOR SEQ ID NO:16:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:16:

CGGAATTCAA TAAATGGGAA CAG                                                 23

(2) INFORMATION FOR SEQ ID NO:17:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:17:

CGCGAATCCA AGGAAAAGAG ACGC                                                24
```

GENETICALLY ENGINEERED YEAST WITH MODIFIED SIGNAL PEPTIDASE COMPLEX The present application is a 35 U.S.C. § 371 national phase application filed from international patent application PCT/US 97/17597, filed Sep. 25, 1997, which claims priority to U.S. Provisional Application Ser. No. 60/026,674, filed Sep. 25, 1996, both of which are hereby incorporated herein by reference in their entirety.

BACKGROUND OF THE INVENTION

1. Field of the Invention

The present invention provides a genetically engineered yeast cell comprising a eukaryotic homologue of a yeast signal peptidase complex subunit. Specifically, this invention provides a yeast cell having functional subunits of the yeast signal peptidase complex, comprising eukaryotic homologues of the yeast Sec11p, Spc1p, Spc2p and Spc3p subunits. The yeast cells can also lack one or more functional subunits of the yeast signal peptidase complex and comprise eukaryotic homologues of the yeast Sec11p, Spc1p, Spc2p and Spc3p subunits. Methods for constructing these yeast cells as well as methods for production of heterologous proteins in these yeast cells are also provided.

2. Background Art

Signal peptidase complex (SPC) in the endoplasmic reticulum (ER) functions in the cleavage of N-terminal signal peptides from proteins that are in transit across the ER membrane (4,39). This almost immediate recognition of translocating polypeptides is critical in maintaining homeostasis in all eukaryotic cells. Despite the importance of the signal peptide cleavage reaction, surprisingly little is known concerning the function of each subunit. The partially purified SPC from yeast appears to contain four subunits, known as Sec11p, Spc1p, Spc2p and Spc3p (13,61) (Table 1).

Genetic and biochemical analyses have demonstrated that (i) Sec11p genetically interacts with Spc1p, Spc2p, and Spc3p; (ii) Sec11p is essential for growth, signal peptidase activity and protein degradation (6,33); (iii) a "core complex" containing Sec11p and Spc3p is sufficient for cell growth and signal sequence cleavage in vivo; and (iv) although not essential for cell growth, Spc1p is important for efficient signal peptidase activity and Spc2p is important for signal peptidase activity and cell viability at high temperatures.

Protein purification studies in other eukaryotic systems have shown that a multisubunit SPC is also present in canine cells (11). The complementary DNAs (cDNAs) encoding all five canine subunits have been cloned and sequenced (19, 20,26,45,46). As shown in Table 2, the yeast subunit, Sec11p, is homologous to SPC18 and SPC21 of the mammalian SPC, yeast subunit Spc1p is homologous to mammalian SPC12, yeast subunit Spc2p is homologous to mammalian SPC25 and yeast subunit Spc3p is homologous to mammalian SPC22/23. The yeast and canine homologues display similarities in their sequences, isoelectric points, and hydropathy profiles as determined by the method of Kyte and Doolittle (30).

SPC purified from avian cells contains only two subunits (p19 and gp23), which are homologous to Sec11p and SPC22/23 (a glycoprotein), respectively (2,35). Unlike the situation in eukaryotes, bacterial leader peptidase contains a single polypeptide with a MW of 36 kDa (63). Leader peptidase is related to Sec11p, SPC18 and SPC21 in that these proteins contain three regions of sequence homology (3,7,54). Because leader peptidase catalyzes signal peptide cleavage as a monomer, these regions of homology may represent all or part of the catalytic site in eukaryotic signal peptidase. As used herein, "catalytic site" means the three regions (domains) of sequence homology which are recognized in the art to be the "consensus sequence" of a eukaryotic signal peptidase. Specifically, the consensus sequence is described in Dalby et al. as the three most highly conserved domains shown in FIG. 4 of Dalby et al.

The yeast *Saccharomyces cerevisiae* has become increasingly popular for the expression and secretion of foreign proteins in pharmaceutical and biotechnology industries for the following reasons: (i) yeast and humans possess similar cellular machinery for the expression and the proper modification of heterologous eukaryotic gene products; and (ii) yeast can be grown economically. However, processing of mammalian signal sequences in yeast is often inefficient. To solve this problem, yeast expression vectors containing one of several yeast signal sequences (e.g., α factor, CPY, invertase, etc.) upstream of mammalian genes are currently being used to obtain more efficient processing. This approach has limited success due to the fact that the efficient processing of mature heterologous proteins by the yeast signal peptidase can be affected by sequences on the carboxyl side of the cleavage site (25).

The present invention overcomes these limitations by providing a yeast cell comprising eukaryotic signal peptidase subunits homologous to the yeast SPC subunits, that process mammalian signal sequences more efficiently than yeast SPC, thereby increasing production of the heterologous proteins in these genetically engineered cells. Thus, the yeast cells of the present invention are improved hosts for heterologous expression and secretion of mammalian proteins than currently available yeast strains.

SUMMARY OF THE INVENTION

The present invention provides a yeast cell comprising a nucleic acid functionally encoding a eukaryotic (e.g., mammalian) protein homologue of a subunit (Sec11p, Spc1p, Spc2p and/or Spc3p) of the yeast signal peptidase complex. The yeast cell of this invention can be, for example, of the genus Saccharomyces, Schizosaccharomyces, Pichia, Hansenula, Kluyveromyces and/or Yarrowia. Furthermore, the yeast cell can lack one or more functional subunits (Sec11p, Spc1p, Spc2p and/or Spc3p) of the yeast signal peptidase complex.

The present invention further provides a method for producing a protein heterologous to a yeast cell comprising expressing, in the yeast cell of this invention, a nucleic acid functionally encoding the heterologous protein under conditions which permit the expression of the nucleic acid as a precursor protein having a signal peptide and processing of the precursor protein to a signal peptide-cleaved form of the protein.

A method is also provided for obtaining increased production of a protein heterologous to a yeast cell comprising expressing, in the yeast cell of this invention, a nucleic acid functionally encoding the heterologous protein under conditions which permit the expression of the nucleic acid as a precursor protein having a signal peptide and processing of the precursor protein to a signal peptide-cleaved form of the protein.

Furthermore, the present invention provides a method for producing a yeast cell capable of producing a protein heterologous to the yeast cell, comprising introducing into the yeast cell (with or without one or more functional SPC subunits) a nucleic acid which functionally encodes one or more eukaryotic protein homologues of a subunit of the yeast signal peptidase complex under conditions permitting the expression of the nucleic acid as the protein homologues.

Additionally provided is a method for producing a yeast cell capable of increased production of a protein heterologous to the yeast cell, comprising introducing into the yeast cell (with or without one or more functional SPC subunits) a nucleic acid which functionally encodes one or more eukaryotic protein homologues of the signal peptidase complex under conditions permitting the expression of the nucleic acid as the protein homologues.

Various other objectives and advantages of the present invention will become apparent from the following description.

DETAILED DESCRIPTION OF THE PREFERRED EMBODIMENTS

The present invention may be understood more readily by reference to the following detailed description of specific embodiments and the Examples included herein. As used in the claims, "a" can include multiples.

The present invention provides a yeast cell comprising a nucleic acid The subunit of the SPC can be Sec11p, Spc1p, Spc2p and/or Spc3p. The yeast cell of this invention can comprise a nucleic acid encoding a subunit homologue of the yeast SPC subunit from, for example, mammals, birds, fish, reptiles, amphibians, arthropods, plants, fungi and other eukaryotic organisms possessing a multisubunit SPC. The yeast cell comprising a nucleic acid encoding a subunit homologue of the yeast SPC subunit can contain all of the yeast SPC subunits in functional form or the yeast cell can lack one or more functional yeast SPC subunits.

Examples of eukaryotic subunit homologues which can be present in the yeast cells of this invention include, but are not limited to, the canine subunits SPC12, SPC25, SPC28, SPC21 and SPC 22/23; human SPC12; Sec11p and SPC 18 homologues in rats; SPC22/23 homologue in *Caenorhabditis elegans*; SPC22/23 and SPC18 homologues in chicken, or other eukaryotic SPC subunit homologous to any of the five canine subunits or other eukaryotic subunits. Typically, the species of the subunit homologue selected will correspond to the species of protein desired to be expressed (e.g., a human SPC subunit homologue would be selected for expression of a human protein in the yeast cell). On the basis of the high degree of sequence homology and similarity in function among homologues of various non-yeast eukaryotes as well as among homologues of the yeast SPC subunits of difference yeast genera, it can be predicted that any eukaryotic yeast SPC subunit homologue can be used in this invention in any genus of yeast having a multisubunit signal peptidase complex.

Examples of mammals from which the SPC subunit homologue of this invention can be obtained can include, but are not limited to, human, cow, pig, goat, sheep, mouse, guinea pig, hamster, squirrel, horse, cat, etc. Any human SPC subunit now known or later identified can be determined to be a homologue of a yeast SPC subunit by sequence comparison and functional homology as described herein. Homologue, as used herein, includes modifications or deletions or insertions to the nucleotide sequence and amino acid sequence of the encoded protein that retain the signal peptidase activity. Introduction of a nucleic acid functionally encoding a eukaryotic SPC subunit homologue into a yeast cell is taught in the Examples provided herein.

Yeast cells of the present invention can include, but are not limited to, Saccharomyces species (e.g., *S. cerevisiae; S. carlsbergensis*) Schizosaccharomyces species (e.g., *S. pombi*), Pichia species (e.g., *P. pastoris*, Hansenula species (e.g., *H. polymorpha*), Kluyveromyces species (e.g. *K. lactis*), Yarrowia species (e.g., *Y. lipolytica*) and any other yeast cell genus having a multisubunit SPC in which eukaryotic subunit homologues can be substituted or co-expressed. Yeast cells can be obtained from a variety of commercial sources and research resource facilities, such as, for example, the American Type Culture Collection in Rockville, Md.

In one embodiment, the yeast cell of the present invention can comprise a nucleic acid functionally encoding a eukaryotic subunit homologue of Sec11p of the yeast signal peptidase complex, such as, for example, the canine subunit protein SPC 18, the canine subunit protein SPC21, or a truncated form of the canine subunit protein SPC21, wherein the negative element (described below) has been deleted. The yeast cell can also contain one or more of these subunits in any combination (e.g. SPC18, SPC18 and SPC21, SPC18 and a truncated SPC21; SPC 18, SPC21 and a truncated SPC21, or SPC21 and a truncated SPC21).

The nucleic acid functionally encoding a eukaryotic homologue of a subunit of the yeast SPC can be any nucleic acid that functionally encodes the eukaryotic subunit homologue. To functionally encode a protein (i.e., allow an exogenous nucleic acid to be expressed in the yeast cell), the nucleic acid can include, but is not limited to, expression control sequences, such as an origin of replication, a promoter, regions upstream or downstream of the promoter, such as enhancers that may regulate the transcriptional activity of the promoter, appropriate restriction sites to facilitate cloning of inserts adjacent to the promoter, marker genes which can serve to select for cells containing the nucleic acid or the vector containing the nucleic acid, in addition to necessary information processing sites, such as ribosome binding sites, RNA splice sites, polyadenylation sites and transcription termination sequences, as well as other sequences which may facilitate the expression of the nucleic acid in the yeast cell.

Preferred expression control sequences are promoters derived from GAL1 genes, GAL10 genes, ADH1 genes, metallothionine genes, actin genes, immunoglobulin genes, CMV, SV40, adenovirus, bovine papilloma virus, etc. A nucleic acid encoding a eukaryotic subunit homologue can readily be determined based upon the genetic code for the amino acid sequence of the homologue and many nucleic acid sequences will encode a given eukaryotic subunit homologue. Modifications in the nucleic acid encoding the subunit homologue are also contemplated. Modifications that can be useful are modifications to the sequences controlling expression of the subunit homologue to make production of the subunit homologue inducible or repressible as controlled by the appropriate inducer or repressor. Such means are standard in the art (see, e.g., ref. 42). The nucleic acid can be generated by means standard in the art, such as by recombinant nucleic acid techniques, as described in the Examples herein and by synthetic nucleic acid synthesis or in vitro enzymatic synthesis.

After a nucleic acid encoding a particular eukaryotic subunit homologue, or a region of that nucleic acid [e.g., wherein the nucleic acid encoding the amino acids of the negative element (described below) has been deleted], is constructed, modified, or isolated, that nucleic acid can then be cloned into an appropriate vector, which can direct the in vivo or in vitro synthesis of that nucleic acid. The vector is contemplated to have the necessary functional elements that direct and regulate transcription of the inserted nucleic acid which are well known in the art, as described herein.

The nucleic acid of this invention can be introduced into the yeast cell of the present invention by any method by which nucleic acid can be introduced into a cell. The introduction of exogenous nucleic acid into yeast cells (i.e., transformation) is well known in the art. Yeast cells can be transformed by a variety of standard protocols. For example, such methods can include, but are not limited to, lithium chloride electroporation, lithium acetate transformation, mixing of nucleic acid with yeast spheroplasts created by enzymatic digestion of the cell wall (spheroplast transformation), particle acceleration (64) and any other method for introducing exogenous nucleic acid into a cell now known or later discovered.

The production of heterologous proteins by expression of exogenous nucleic acid in transformed yeast cells in culture is standard in the art and the culture conditions for a given yeast strain would be well known to one of skill in the art. The heterologous protein can be maintained within the yeast cell and released upon cell lysis or the heterologous protein can be secreted into the culture medium via a mechanism provided by a coding sequence (either native to the exogenous nucleic acid or engineered into the expression vector) which directs secretion of the protein from the cell. The presence of the heterologous protein in the cell lysate or culture medium can be verified by a variety of standard protocols for detecting the presence of a protein. Such protocols can include, but are not limited to, Western blotting or radioimmunoprecipitation with an antibody specific for the heterologous protein, binding of a ligand specific for the heterologous protein, specific enzyme activity of the heterologous protein, etc. as would be well known to the artisan.

The exogenous nucleic acid can be in the form of an expression vector which can be a plasmid, phage, transposon, cosmid or virus particle. The exogenous nucleic acid can be maintained extrachromosomally or it can be integrated into the yeast cell chromosomal DNA.

The exogenous nucleic acids are typically replicable in cells either as episomes or as an integral part of the host chromosomal DNA. The nucleic acids encoding the eukaryotic protein homologues can be expressed in yeast cells after the sequences have been positioned, for example, in an expression vector to ensure the functioning of an expression control sequence. Commonly, expression vectors can contain selection marker genes encoding proteins required for cell viability under selected conditions (e.g., URA3, which encodes an enzyme necessary for uracil biosynthesis or TRP1, which encodes an enzyme required for tryptophan biosynthesis) to permit detection and/or selection of those cells transformed with the desired nucleic acids (see, e.g., U.S. Pat. No. 4,704,362).

As used herein, "negative element" means 1) a region of amino acids present in the amino acid sequence of a eukaryotic SPC subunit homologue which is not present in the yeast SPC subunit, 2) which has the negative effect of preventing functional replacement of the yeast SPC subunit by the subunit homologue in yeast cells expressing the homologue; and 3) for which the negative effect is eliminated upon deletion of all or some of the amino acids in this region. For example, the canine subunit protein SPC21 contains a 24 residue amino terminal extension that is not present in the yeast subunit protein, Sec11p. The presence of this amino terminal sequence on SPC21 in yeast cells has the negative effect of preventing functional replacement of Sec11p by SPC21 in cells expressing this homologue. Deletion of the amino terminal 24 amino acids from SPC21 resulted in the functional replacement of Sec11p cells in yeast cells expressing this truncated form of SPC21. As another example, the canine subunit homologue SPC25 contains 25 amino acid residues at its amino terminus that do not exist in its yeast counterpart. All or part of this region can be deleted for functional replacement of Spc2p by SPC25 in a yeast cell.

To identify negative elements in other eukaryotic SPC subunit homologues, the amino acid sequences of the yeast subunits can be compared with the amino acid sequences of other eukaryotic SPC subunit homologues for the detection of amino acid sequences present in the homologues that do not exist in the yeast subunit. Homologues of yeast SPC subunits having additional amino acids which are not present in the yeast SPC subunits can be tested for function according to the methods provided herein If the presence of this unmatched region on the subunit homologue expressed in the yeast cell prevents functional replacement of the corresponding yeast subunit and deletion of all or part of this unmatched region results in the functional replacement of the yeast subunit, as determined according to the methods provided herein, then the deleted region has been identified to be a negative element.

The deletion of amino acids in a negative element region can be carried out according to standard methods known in the art of genetic engineering and protein cleavage. An example of how a truncated form of the canine subunit protein SPC21 can be created is provided in the Examples herein.

The yeast cell of this invention can also comprise a nucleic acid functionally encoding a eukaryotic subunit homologue of Spc3p of the yeast signal peptidase complex, such as for example, the canine subunit SPC22/23.

Additionally, the yeast cell of the present invention can also comprise a nucleic acid functionally encoding a eukaryotic subunit homologue of both subunits Sec11p and Spc3p of the yeast signal peptidase complex. For example, the yeast cell can comprise a nucleic acid encoding SPC18, SPC21 and/or a truncated SPC21, with negative element deleted (as homologues of yeast subunit Sec11p) and nucleic acid encoding SPC22/23 (as homologue of yeast subunit Spc3p), in any combination. The creation of a yeast cell comprising a nucleic acid functionally encoding a eukaryotic protein homologue of subunit Sec11p and subunit Spc3p of the yeast signal peptidase complex is described in the Examples provided herein.

The present invention also provides a yeast cell comprising a nucleic acid functionally encoding a eukaryotic subunit homologue of Spc1p of the yeast signal peptidase complex. For example, the yeast cell can comprise the canine subunit protein, SPC12. In addition, the yeast cell of the present invention can comprise a nucleic acid functionally encoding a eukaryotic subunit homologue of Spc2p of the yeast signal peptidase complex. For example, the yeast cell can comprise the mammalian subunit protein, SPC25. A yeast cell comprising a nucleic acid functionally encoding a eukaryotic subunit homologue of Spc1p and Spc2p is also contemplated. Such a yeast cell can contain, for example, the mammalian protein SPC12 (as homologue of Spc1p) and the mammalian protein SPC25 (as homologue of Spc2p). The yeast cell of the present invention can contain eukaryotic subunit homologues of one, two, three or four of the yeast SPC subunits in any combination with regard to the number of different homologues for a given subunit, the eukaryotic source of the subunit homologue and the presence or absence of a given functional yeast SPC subunit in the yeast cell (as described below).

Also provided is a yeast cell lacking a functional yeast SPC subunit, The yeast cell can lack one, two, three or four functional yeast SPC subunits in any combination. As used herein, a yeast cell lacking a functional SPC subunit is a yeast cell which is naturally occurring or has been genetically engineered such that a gene of the functional subunit which is lacking, has been deleted or has been disrupted so that no complete or functional form of the yeast SPC subunit is present in the yeast cell.

For example, the cell of the present invention can be a yeast cell lacking a functional Sec11p subunit of the yeast signal peptidase complex, wherein the yeast cell comprises a nucleic acid functionally encoding a eukaryotic subunit homologue of Sec11p. A yeast cell lacking a functional Sec11p subunit can be created according to the methods taught herein in the Examples. Such a yeast cell can comprise, for example, the canine subunit protein SPC21; the canine subunit protein SPC18; a truncated form of SPC21, wherein the negative element has been deleted; SPC18 and SPC21 1 SPC 18 and a truncated SPC21; or SPC18, SPC21 and a truncated SPC21.

The present invention also provides a yeast cell lacking a functional Spc3p subunit of the yeast signal peptidase complex, wherein the yeast cell comprises a nucleic acid functionally encoding a eukaryotic subunit homologue of Spc3p, such as, for example, the canine subunit protein SPC22/23. A yeast cell lacking a functional Spc3p subunit can be created according to the methods taught herein in the Examples.

Also provided is a yeast cell lacking both a functional Sec11p unit and a functional Spc3p subunit of the yeast signal peptidase complex, wherein the yeast cell comprises a nucleic acid functionally encoding a eukaryotic subunit homologue of Sec11p and/or Spc3p, respectively. A yeast cell lacking both a functional Sec11p subunit and functional Spc3p subunit can be created according to the methods taught herein in the Examples. Such cells can comprise, for example, a nucleic acid encoding SPC18, SPC21 and/or a truncated SPC21, with negative element deleted (as homologues of yeast subunit Sec11p) and/or nucleic acid encoding SPC22/23 (as homologue of yeast subunit Spc3p), in any combination. The creation of a yeast cell comprising a nucleic acid functionally encoding a eukaryotic protein homologue of subunit Sec11p and subunit Spc3p of the yeast signal peptidase complex is described in the Examples provided herein.

The yeast cell of the present invention can also lack a functional Spc1p subunit, a functional Spc2p subunit or both a functional Spc1p subunit and functional Spc2p subunit. Methods for making a yeast cell lacking a functional Spc1p subunit and/or a functional Spc2p subunit are provided in the Examples herein. Such cells can comprise, for example, nucleic acids functionally encoding mammalian subunit proteins SPC12, SPC25 or SPC12 and/or SPC25. It is also contemplated that the present invention provides yeast cells lacking functional yeast SPC subunits in any and all combinations and comprising substituted and/or co-expressed eukaryotic subunit homologues in any and all corresponding combinations.

Furthermore, the present invention provides a method for producing a protein heterologous to a yeast cell comprising expressing, in a yeast cell of the present invention, a nucleic acid functionally encoding the heterologous protein under conditions which permit the expression of the nucleic acid as a precursor protein having a signal peptide and processing of the precursor protein into a signal peptide-cleaved form of the protein. Purification of the heterologous protein from a cell lysate or culture medium, if desired, can be carried out according to isolation and purification protocols well known in the art.

It is contemplated that the yeast cells of the present invention can produce increased levels of the heterologous protein in comparison to the levels of heterologous proteins produced in yeast cells comprising only yeast SPC subunits with no eukaryotic protein homologues in the cell. Thus, the present invention further provides a method for obtaining increased production of a protein heterologous to a yeast cell comprising expressing, in a yeast cell of the present invention, a nucleic acid functionally encoding the heterologous protein under conditions which permit the expression of the nucleic acid as a precursor protein having a signal peptide and processing of the precursor protein into a signal peptide-cleaved form of the protein.

As described herein, the yeast cell of this invention can comprise 1) a nucleic acid functionally encoding a eukaryotic subunit homologue of Sec11p; 2) a nucleic acid functionally encoding a eukaryotic subunit homologue of Spc3p; 3) a nucleic acid functionally encoding a eukaryotic subunit homologue of Sec11p and Spc3p; 4) a nucleic acid functionally encoding a eukaryotic subunit homologue of Spc1p; 5) a nucleic acid functionally encoding a eukaryotic subunit homologue of Spc2p; and/or 6) a nucleic acid functionally encoding a eukaryotic subunit homologue of Spc1p and Spc2p.

As used herein, a protein heterologous to the yeast cell is any protein which is not naturally produced in the yeast cell or which is encoded by a nucleotide sequence which does not originate in the yeast cell and is therefore foreign to the yeast cell. As used herein, "processing of the precursor protein" means the post translational modifications made to the protein (i.e., glycosylation, acylation, disulfide bond formation), as well as proteolytic cleavage of the signal sequence, to yield the signal peptide-cleaved form of the protein, as the protein is synthesized and transported via the ER and Golgi apparatus to its final destination either within or outside of the cell.

The yeast cell of the above-described methods can contain a nucleic acid encoding one or more eukaryotic subunit proteins which are homologues of the yeast SPC subunits Sec11p, Spc1p, Spc2p or Spc3p, in any combination, such as, for example, SPC22/23 and/or SPC 18; SPC22/23 and/or SPC21; SPC22/23 and/or a truncated SPC21, wherein the negative element has been deleted; SPC22/23, SPC 18 and/or SPC21; SPC22/23, SPC18 and/or a truncated SPC21; SPC22/23, SPC 18, SPC21 and/or a truncated SPC21 and/or SPC25 and/or SPC12.

The yeast cell of this method can comprise a nucleic acid functionally encoding a heterologous protein such as, for example, growth factors (e.g., insulin-like growth factor-1, epidermal growth factor); interferons (e.g., human interferon-alpha, human interferon-beta, human interferon-gamma); protease inhibitors (e.g., human pancreatic secretory trypsin inhibitor, also known as human antitrypsin); antigens (e.g., hepatitis B virus antigens; influenza virus hemagglutinin; herpes simplex virus glycoprotein B. Epstein Barr virus glycoprotein; human immunodeficiency virus envelope glycoprotein); and hormones (e.g., preproinsulin), as well as any other heterologous protein, containing a signal peptide, that can be expressed in a yeast cell.

The present invention additionally provides a method for producing a protein heterologous to a yeast cell comprising expressing, in a yeast cell of the present invention, a nucleic acid functionally encoding the heterologous protein under conditions which permit the expression of the nucleic acid as a precursor protein having a signal peptide and processing of the precursor protein into a signal peptide-cleaved form of the protein, wherein the yeast cell can lack either 1) a functional Sec11p; 2) a functional Spc3p; or 3) a functional Sec11p and Spc3p and can comprise either 1) a nucleic acid functionally encoding a eukaryotic protein homologue of Sec11p; 2) a nucleic acid functionally encoding a eukaryotic protein homologue of Spc3p; or 3) a nucleic acid functionally encoding a eukaryotic protein homologue of Sec11p and Spc3 p. The yeast cell can comprise, for example, mammalian subunit proteins SPC22/23 and/or SPC18; SPC22/23 and/or a truncated SPC21, wherein the negative element has been deleted; SPC22/23, SPC18 and/or SPC21; SPC22/23, SPC 18 and/or a truncated SPC21; or SPC22/23, SPC18, SPC21 and/or a truncated SPC21.

The present invention additionally provides a method for producing a protein heterologous to a yeast cell comprising expressing, in a yeast cell of the present invention, a nucleic acid functionally encoding the heterologous protein under conditions which permit the expression of the nucleic acid into a precursor protein having a signal peptide and processing of the precursor protein into a signal peptide-cleaved form of the protein, wherein the yeast cell can lack either 1) a functional Spc1p; 2) a functional Spc2p; or 3) a functional Spc1p and Spc2p and/or can comprise either 1) a nucleic acid functionally encoding a eukaryotic subunit homologue of Spc1p; 2) a nucleic acid functionally encoding a eukaryotic subunit homologue of Spc2p; or 3) a nucleic acid functionally encoding a eukaryotic subunit homologue of Spc1p and Spc2p. The yeast cell can comprise, for example, mammalian subunit proteins SPC12, SPC25 or SPC12 and/or SPC25.

A method is also provided for obtaining increased production of a protein heterologous to a yeast cell comprising expressing, in a yeast cell of the present invention, a nucleic acid functionally encoding the heterologous protein under conditions which permit the expression of the nucleic acid into a precursor protein having a signal peptide and processing of the precursor protein into a signal peptide-cleaved form of the protein, wherein the yeast cell can lack either 1) a functional Sec11p; 2) a functional Spc3p, or 3) a functional Sec11p and Spc3p and can comprise either 1) a nucleic acid functionally encoding a eukaryotic subunit homologue of Sec11p, 2) a nucleic acid functionally encoding a eukaryotic subunit homologue of Spc3p; or 3) a nucleic acid functionally encoding a eukaryotic subunit homologue of Sec11p and Spc3p. The yeast cell can comprise, for example, mammalian subunit proteins SPC22/23 and/or SPC18; SPC22/23 and/or a truncated SPC21, wherein the negative element has been deleted, SPC22/23, SPC 18 and/or SPC21; SPC22/23, SPC18 and/or a truncated SPC21; or SPC22/23, SPC 18, SPC21 and/or a truncated SPC21.

The present invention further provides a method for obtaining increased production of a protein heterologous to a yeast cell comprising expressing, in a yeast cell of the present invention, a nucleic acid functionally encoding the heterologous protein under conditions which permit the expression of the nucleic acid into a precursor protein having a signal peptide and processing of the precursor protein into a signal peptide-cleaved form of the protein, wherein the yeast cell can lack either 1) a functional Spc1p, 2) a functional Spc2p; or 3) a functional Spc1p and Spc2p and/or can comprise either 1) a nucleic acid functionally encoding a eukaryotic subunit homologue of Spc1p; 2) a nucleic acid functionally encoding a eukaryotic subunit homologue of Spc2p; or 3) a nucleic acid functionally encoding a eukaryotic subunit homologue of Spc1p and Spc2p. The yeast cell can comprise, for example, mammalian subunit proteins SPC12, SPC25 or SPC12 and/or SPC25.

A method for producing a yeast cell capable of expressing a nucleic acid functionally encoding a protein heterologous to the yeast cell is also provided, comprising introducing into the yeast cell a nucleic acid which functionally encodes any eukaryotic subunit homologue of Sec11p and/or Spc3p of the yeast signal peptidase complex under conditions permitting the expression of the nucleic acid as the subunit homologue or homologues. The yeast cell of this method can comprise, for example, a nucleic acid which functionally encodes mammalian subunit proteins SPC22/23 and/or SPC18; SPC22/23 and/or SPC21; SPC22/23 and/or a truncated SPC21, wherein the negative element has been deleted, SPC22/23, SPC18 and/or SPC21, SPC22/23, SPC18 and/or a truncated SPC21, or SPC22/23, SPC 8, SPC21 and/or a truncated SPC21.

Furthermore, the present invention provides a method for producing a yeast cell capable of expressing a nucleic acid of a protein heterologous to the yeast cell, comprising introducing into a yeast cell lacking a functional Sec11p subunit and/or a functional Spc3p subunit of the yeast signal peptidase complex a nucleic acid which functionally encodes a eukaryotic subunit homologue of Sec11p and/or Spc3p under conditions permitting the expression of the nucleic acid as the subunit homologue or homologues. The yeast cell of this invention can comprise, for example, nucleic acid functionally encoding mammalian subunit proteins SPC22/23 and/or SPC18; SPC22/23 and/or a truncated SPC21, wherein the negative element has been deleted; SPC22/23, SPC18 and/or SPC21; SPC22/23, SPC18 and/or a truncated SPC21; or SPC22/23, SPC 18, SPC21 and/or a truncated SPC21.

A method for producing a yeast cell capable of expressing a nucleic acid functionally encoding a protein heterologous to the yeast cell is also provided, comprising introducing into the yeast cell a nucleic acid which functionally encodes a eukaryotic subunit homologue of Spc11p and/or Spc2p of the yeast signal peptidase complex under conditions permitting the expression of the nucleic acid as the subunit homologue or homologues. The yeast cell of this method can comprise, for example, mammalian subunit proteins SPC12, SPC25, or SPC12 and/or SPC25.

Furthermore, the present invention provides a method for producing a yeast cell capable of expressing a nucleic acid of a protein heterologous to the yeast cell, comprising introducing into a yeast cell lacking a functional Spc1p subunit and/or a functional Spc2p subunit of the yeast signal peptidase complex, a nucleic acid which functionally encodes a eukaryotic subunit homologue of Spc1p and/or Spc2p under conditions permitting the expression of the nucleic acid as the subunit homologue or homologues. The yeast cell of this invention can comprise, for example, mammalian subunit proteins SPC12, SPC25, or SPC12 and/or SPC25.

The yeast cells of the methods described above, having functional yeast SPC subunits, can comprise eukaryotic subunit homologues in any and all combinations. In addition, the yeast cells of these methods lacking functional yeast SPC subunits in any and all combinations can comprise nucleic acid encoding eukaryotic subunit homologues in any and all combinations. For example, the yeast cells can lack a functional Sec11p subunit and a functional Spc2p subunit, or a functional Sec11p subunit and a functional Spc1p subunit, or a functional Sec11p subunit, a functional Spc1p subunit and a functional Spc3p subunit, as well as any other combination. The yeast cells can comprise, for example, SPC18 and SPC12, SPC12, a truncated SPC21 and SPC25 or SPC 18, SPC21 and a nonmammalian eukaryotic subunit homologue to Sec11p, Spc1p, Spc2p or Spc3p, as well as any other combination.

The present invention is more particularly described in the following examples which are intended as illustrative only since numerous modifications and variations therein will be apparent to those skilled in the art.

EXAMPLES

Plasmid constructs bearing the SPC3 gene. Plasmid pSPC3 bearing SPC3 was isolated from a high copy (2 μm) plasmid library marked with LEU2 (ATCC No. 37323). Among 5,500 transformants of strain CMYD1 (sec11-7), pSPC3 was isolated from one colony that grew at 32° C. The SPC3 gene was amplified from pSPC3 by PCR using the forward oligonucleotide primer CGGGATCCACACGT-GAATACTACC (SEQ ID NO:15), which is located 204 bp upstream of the SPC3 start codon, and the reverse primer CGGAATTCAATAAATGGGAACAG (SEQ ID NO:16), which is located 189 bp downstream of the SPC3 stop codon. The amplified fragment was restricted with BamHI and EcoRI and inserted into a low copy (CEN) plasmid pRS314 (TRPI) (21). The resulting plasmid was named pHF332. A 1.5 kb HindIII-XbaI restriction fragment containing the SPC3 gene was excised from plasmid pSPC3 and inserted into 2 μm plasmid pRS426 (71). The resulting plasmid was named pHF931.

Construction of yeast cells lacking functional Sec11p and Spc3p subunits. A strain of yeast cells containing Δsec11 Δspc3 (Δsec11::HIS3 Δspc3::LEU2) mutations, chromosomally located, was constructed by disrupting these two genes according to methods described previously (13,14). Briefly, the 1.5 kb HindIII-XbaI restriction fragment containing the SPC3 gene was inserted into the polylinker of pUC19 (72). The resulting plasmid was restricted with NHEI, which cuts 30 bp upstream of the SPC3 open reading frame and SPEI, which cuts 3 bp downstream of the stop codon of SPC3. The SPC3 gene was replaced with a 1.6 kb NheI DNA fragment containing the LEU2 gene. This NheI fragment was obtained from a modified YDp-L plasmid (73) that contains LEU2 flanked by two NheI sites (a NheI linker was inserted at the SmaI site of YDp-L). This construct containing a replacement of SPC3 with the LEU2 gene was restricted with HindIII and XbaI and transformed into diploid strain SEY6210.5 (1) with selection for leucine prototrophs. Homologous recombination of the sequences flanking the SPC3 disruption produced diploid cells containing the heterozygous disruption of the SPC3 gene. Transformants bearing a replacement of the SPC3 gene with the LEU2 gene were confirmed by genomic PCR using oligonucleotide primers described above.

The SEC11 gene, which encodes Sec11p, was similarly deleted from the chromosome of diploid yeast cells except that the HIS3 gene was inserted between two SnaBI sites that flank the SEC11gene.

Both SPC3 and SEC11 are essential genes. Diploid cells bearing heterozygous disruptions of these genes are viable because these cells contain one good copy of each gene. However, haploid cells bearing disruptions of either or both genes are nonviable. Therefore, before sporulating the heterozygous diploid cells, a plasmid containing SPC3 and SEC11 genes must be introduced into cells. SPC3 (HindIII - XbaI fragment) and SEC11 (BamHI-SacI fragment) genes were cloned onto plasmid pRS316 (25). This plasmid carries the URA3 marker gene (which encodes an enzyme required for uracil biosynthesis). It is important to use a marker that can be selected against in order to eliminate this plasmid at a later step. Heterozygous SPC3 disruption strain and heterozygous SEC11 disruption strain were transformed with the plasmid bearing SPC3 and SEC11 and then subjected to sporulation. Haploid cells bearing the disruption of SPC3 (marked by Leu+ phenotype) and distinct haploid cells bearing the disruption of SEC11 (marked by His+ phenotype) were obtained. These cells also contained the plasmid bearing SEC11 and SPC3 (marked by their viability and Ura+ phenotype). To make cells containing both disruptions, different strains containing these disruptions were checked for mating type (either MATa or MATalpha) using tester strains of defined mating type. Strains containing the disruptions of SPC3 and SEC11 were identified of the opposite mating type. Having identified such strains, cells were mated, thus producing diploid cells containing a heterozygous disruption of SPC3 and SEC11. The plasmid bearing SPC3 and SEC 11 was maintained in these diploid cells through selection for the URA3 marker. Diploid cells were then allowed to sporulate and haploid cells phenotypically Leu+, His+ and Ura+ were identified. These cells contained a disruption of SPC3 and a disruption of SEC11. Their viability was ensured because cells contained a plasmid bearing the SPC3 and SEC 11 genes.

Construction of yeast cells lacking functional Spc1p and Spc2p. The plasmid used for disruption of SPC1 was constructed as follows. The 2.3 kb EcoRI fragment containing SPC1, which encodes Spc1p (17), was inserted into vector pUC19 (65). The resulting plasmid was digested with SpeI, which removes the entire SPC1 coding region. A 0.8 kb NheI fragment containing the TRP1 gene was inserted into this SpeI site. The NheI fragment was obtained from a modified YAP-W plasmid (66) that contains TRP1 flanked by two NheI sites (a NheI linker was inserted at the SmaI site of the plasmid YAP-W). This construct was linearized by digestion with EcoRI, then transformed into diploid strain SEY6210.5 (1). Selection for the disruption mutation was performed on minimal agar plates supplemented appropriately but lacking tryptophan.

The construct used for disruption of SPC2, which encodes Spc2p, was produced as described (17). Genomic SPC2 of strain NGY21B was amplified through PCR using forward primer GTTGATCATCATCTTAGA (SEQ ID NO:1) and reverse primer CGACGTGCTGTATAATGA (SEQ ID NO:2), that flank the coding sequence. The reaction was carried out using a GENE AMP kit according to manufacturer's specifications (Perkin Elmer Cetus, Norwalk, Conn.). The amplified fragment (1.8 kb) was restricted with BglII and NsiI. The BglII-NsiI restriction fragment was inserted into modified pRS315 (68) (lacking the HindIII site) at BamHI and PstI sites. The resulting plasmid contained two HindIII sites located within the SPC2 coding sequence. A 1.2 kb HindIII fragment containing the URA3 gene was inserted into these HindIII sites, resulting, in the deletion of a 0.2 kb sequence of the SPC2 gene. This construct was linearized with SpeI and XhoI and transformed into diploid strain SEY6210.5. Selection for the disruption mutation was performed on minimal agar plates supplemented appropriately but lacking uracil (18).

Plasmid pHF324 containing the GAL1/GAL10 divergent promoter fragment (24) followed by the SPC2 gene was constructed as follows. The SPC2 gene was amplified by PCR using a forward oligonucleotide-bearing BamHI site upstream of the start codon of SPC2, CGCGAATCCAAG-GAAAAGAGACGC (SEQ ID NO:17) and the above-described reverse primer, which is located 260 nucleotides downstream of the SPC2 stop codon. The PCR product was digested with BamHI and NsiI and the resulting DNA fragment was cloned into pRS315 (21) at the BamHI and PstI sites. A 0.7 kb BamHI fragment bearing the GAL1/GAL10 promoter (13) was inserted into the BamHI site upstream of SPC2. The SPC2 gene was inserted into a 2 μm plasmid as follows. The BglII-NsiI DNA fragment containing SPC2 was cloned into pRS425 (71) at the BamHI-PstI sites.

To verify construction of the SPC1 and SPC2 mutations, genomic DNA was isolated from yeast cells according to previously described methods (69) and subjected to Southern blotting (70).

Upon selection for Ura+ and Trp+ prototrophs of strain SEY6210.5 bearing heterozygous disruptions of SPC1 or SPC2, diploid cells are sporulated and subjected to tetrad analysis. Ura+ haploid cells bearing a disruption of SPC2 and Trp+ haploid cells bearing a disruption of SPC1 are obtained. These cells are viable since SPC1 and SPC2 are nonessential for yeast cell growth.

Alternatively, to introduce SPC1 and SPC2 disruptions into haploid strains carrying one or more eukaryotic homologues of signal peptidase subunits, the disruptions can be directly made in these strains using the methods described above. The only provision is that the strains employed contain nonrevertable mutations in URA3 and TRP1 genes (deletion of these genes in the strains is preferable).

Cloning and expression of mammalian SPC12, SPC18, SPC21, SPC22/23 and SPC25 in yeast cells. To clone the mammalian signal peptidase subunit genes encoding SPC18, SPC21, SPC22/23 and SPC25, the sequences of which are known (19,20,26,45,46), total RNA was prepared from canine spleen. The SPC12 gene was amplified from fetal human brain RNA as described (26). RT-PCR was performed using a kit from Clontech. Briefly, first strand synthesis was performed using random hexamer primers and Moloney murine leukemia virus reverse transcriptase. The SPC 12, SPC18, SPC21, SPC22/23 and SPC25 genes were amplified by PCR reactions using the forward oligonucleotide and reverse oligonucleotide primers described in Table 3. The PCR products were purified by phenol extraction, precipitated and subsequently digested with appropriate restriction enzymes (BamHI +EcoRI for SPC12, SPC18, SPC21 and SPC25 and BamHI +ClaI for SPC22/23). The PCR-derived sequences were verified by DNA sequencing from M13-based vectors. The digested DNA fragments were inserted into the appropriate sites of vector pRS314 (CEN, TRP1) (25). A 1.5 kb BamHI fragment bearing the ADH1 promoter (22) was inserted into the plasmid at the BamHI site immediately upstream of the SPC genes. This BamHI promotor fragment was obtained from the plasmid pNG107 described previously (18). ADH1 is a yeast promotor that permits expression of foreign proteins in yeast, however, other promoters, such as the GAL1 promotor (24), can be used.

Replacement of Sec11p with mammalian SPC proteins in yeast Δsec11 mutant. A series of Δsec11 mutants bearing a URA3-marked plasmid containing the wild-type SEC11 gene (pSEC11-URA3) and bearing no additional plasmid, or a TRP1-marked plasmid containing either the SEC11 (pSEC11-TRP1), spc18 (pSPC18-TRP1), spc21(pSPC21 -TRP1), or spc21ΔN (pSPC21ΔN-TRP1) genes were grown to log phase ($A_{600}$=1) in a medium selecting for these plasmids. Ten μl of cells was placed on a SC-CAS (18) agar plate supplemented with uracil and 5'-fluoroorotic acid, the latter of which selects against cells bearing a URA3-marked plasmid (5). Through employment of the plasmid shuffle technique (5), SPC18 was found to functionally replace Sec11p in a Δsec11 mutant. In contrast, SPC21 did not replace Sec11p as measured by a cell growth assay, indicating that SPC18 and SPC21 are not functionally equivalent as measured in yeast cells.

The mammalian protein SPC22/23 did not replace its yeast homologue Spc3p in cells containing all the other yeast subunits as indicated by a growth assay. However, yeast cells containing mammalian SPC 18 and SPC22/23 but lacking Sec11p and Spc3p were viable, indicating that these yeast strains utilize a two-subunit mammalian SPC for signal peptidase activity and cell growth. This "core" complex contains SPC18 and SPC22/23.

Cloning of SPC21DN, encoding a truncated form of SPC21 wherein the negative element has been deleted. SPC 18, which does not contain an amino acid region that does not exist in its yeast counterpart, Sec11p, was able to functionally replace Sec11p in yeast cells in which a nucleic acid encoding this subunit homologue was expressed. In contrast, SPC21, which contains a 24 amino acid region at its amino terminus which does not exist in its yeast counterpart, Sec11p, did not functionally replace Sec11p in yeast cells in which a nucleic acid encoding this protein homologue was expressed. Therefore, to determine if this unmatched extension prevented functional replacement of Sec11p by SPC21, a construct was prepared comprising a gene, SPC21DN, encoding a truncated form of SPC21, in which the amino terminal 24 amino acids had been deleted. To clone SPC21DN, the following nucleotides were used to amplify DNA encoding SPC21DN from SPC21 DNA that was already cloned:

Forward primer: 5'-CGGGATCCATGAACAAGCGGCAG-3' (SEQ ID NO:3)

Reverse primer: 5'-GGGGAATTCTCTTTTTAGGATTCACGT-3' (SEQ ID NO:4)

The PCR product was purified by phenol extraction and precipitated and subsequently digested with appropriate restriction enzymes (BamHI and EcoRI). The digested DNA fragments were inserted into the appropriate sites of vector pRS314 (CEN, TRP1) (25). A 1.5 kb fragment bearing the ADH1 promoter (22) was inserted into the plasmid at the BamHI site immediately upstream of the SPC genes. This BamHI promoter fragment was obtained from the plasmid pNG107 described previously (18). The final construct placed Met25 of SPC21 immediately downstream of the ADH1 promoter.

Expression of foreign genes in yeast cells comprising eukaryotic homologues of yeast SPC subunits. Nucleic acids encoding proteins heterologous to yeast cells can be expressed in yeast cells (with or without functional SPC subunits) comprising eukaryotic protein homologues of subunits of the yeast signal peptidase complex using a number of published vectors for foreign gene expression in yeast (8,22). Conditions for expression of the nucleic acids encoding the heterologous proteins in the yeast cell and the purification of the heterologous proteins from the yeast expression system are well known in the art. Expression can be mediated from plasmids or from chromosomally located genes. For plasmid expression, a variety of promoters can be used such as the fairly constitutive promotor (ADH1) (22) or the regulated promotor GAL1 (24). For chromosomal expression, the gene of interest can be cloned into a yeast integrative plasmid (8).

Various eukaryotic proteins, such as human α-antitrypsin (23) and human interferons (IFN-α2, IFN-β1) (25,40) can be expressed in the yeast cells of this invention. Nucleic acid encoding the heterologous protein can be obtained from commercially available cDNA libraries and amplified by PCR. The gene product can be expressed by cloning into the yeast expression vectors described herein. The amount of the eukaryotic protein in the cell and in the medium can be monitored by techniques such as Western blot analysis or immunoprecipitation with commercially available antibodies according to protocols well known in the art. The heterologous protein can be isolated and purified from the culture supernatant or cell extract according to methods well known in the art.

Throughout this application, various publications are referenced. The disclosures of these publications in their entireties are hereby incorporated by reference into this application in order to more fully describe the state of the art to which this invention pertains.

Although the present invention has been described with reference to specific details of certain embodiments thereof, it is not intended that such details should be regarded as limitations upon the scope of the invention except as and to the extent that they are included in the accompanying claims.

REFERENCES

1 Herman, P. K., and Emr, S. D. (1990). Characterization of VPS, a gene required for vacuolar protein sorting and vacuole segregation in *Saccharomyces cerevisiae*. Mol. Cell. Biol. 10,6742–6754.

2 Baker, R. K. and Lively, M. O. (1987). Purification and characterization of hen oviduct microsomal signal peptidase. Biochemistry 26, 8561–8567.

3 Bilgin, N., Lee, J. I., Zhu, H., Dalbey, R., and von Heijne, G. (1990). Mapping of catalytically important domains in *Escherichia coli* leader peptidase. EMBO J. 9, 2717–2722.

4 Blobel, G., and Dobberstein, B. (1975). Transfer of proteins across membranes I. Presence of proteolytically processed and unprocessed nascent immunoglobulin light chains on membrane-bound ribosomes of murine myeloma. J. Cell Biol. 67, 835–851.

5 Boeke, J., Trueheart, J., Natsoulis, G., and Fink, G. (1987). 5-Fluoroorotic acid as a selective agent in yeast molecular genetics. Meth. Enzymol. 154, 164–175.

6 Bohni, P. C., Deshaies, R. J., and Schekman, R. W. (1988). SEC11 is required for signal peptide processing and yeast cell growth. J. Cell Biol. 106, 1035–1042.

7 Dalbey, R. E. and von Heijne, G. (1992). Signal peptidases in prokaryotes and eukaryotes—a new protease family. TIBS 17, 474–478.

8 Botstein, D., and Davis, R. W. Principles and practice of recombinant DNA research with yeast in The Molecular Biology of the Yeast Saccharomyces Metabolism and Gene Expression. Cold Spring Harbor Laboratory, 1982, pp. 607–636.

11 Evans, E. A., Gilmore, R., and Blobel, G. (1986). Purification of microsomal signal peptidase as a complex. Proc. Natl. Acad. Sci. U.S.A. 83, 581–585.

13 Fang, H., Panzner, S., Mullins, C., Hartmann, E., Green, N. (1996). The homologue of mammalian SPC12 is important for efficient signal peptidase activity in *Saccharomyces cerevisiae*. J. Biol. Chem. 271, 16460–16465.

14. Fang, H., Mullins, C. and Green, N. (May 16, 1997) In addition to SEC11, a newly identified gene, SPC3, is essential for signal peptidase activity in the yeast endoplasmic reticulum. J. Biol. Chem. 272, 13152–13158.

16 Gorlich, D. and Rapoport, T. A. (1993). Protein translocation into proteoliposomes reconstituted from purified components of the endoplasmic reticulum membrane. Cell 75, 615–630.

17. Mullins, C., Meyer, H.-A., Hartmann, E, Green, N. and Fang, H. (Nov. 16, 1997) Structurally related spc1p and spc2p of yeast signal peptidase complex are functionally distinct. J. Biol. Chem. 271, 29094–29099.

18 Green, N. and Walter, P. (1992). C-terminal sequences can inhibit the insertion of membrane proteins into the endoplasmic reticulum of *Saccharomyces cerevisiae*. Mol. Cell. Biol. 12, 276–282.

19 Greenburg, G., and Blobel, G. (1994). cDNA-derived primary structure of the 25-kDa subunit of canine microsomal signal peptidase complex. J. Biol. Chem. 269, 25354–25358.

20 Greenburg, G., Shelness, G. S., and Blobel, G. (1989). A subunit of mammalian signal peptidase is homologous to yeast Sec11 protein. J. Biol. Chem. 264, 15762–15765.

21 Sikorski, R. S. and Hieter, P. (1989) Genetics 122,19–27.

22 Henikoff, S., and Furlong, C. E. (1983). Sequence of a Drosophila DNA segment that functions in *Saccharomyces cerevisiae* and its regulation by a yeast promotor. Nucl. Acids Res. 11, 789–800.

23 Cabeqon, T., DeWilde, M., Herion, P., Lorian, R., and Bollen, A. (1984) Expression of human $\alpha_1$-antitrypsin cDNA in the yeast *Saccharomyces cerevisiae*. Proc. Natl. Acad. Sci. U.S.A. 81, 6594–6598.

24 Johnston, M. and Davis, R. W. (1984). Sequences that regulate the divergent GAL1–GAL10 promoter in *Saccharomyces cerevisiae*. Mol. Cell. Biol. 4, 1440–1448.

25 Piggott, J. R., Watson, M. E., Doel, S. M., Goodey, A .R., and Carter, B. L. (1987) The secretion and post translational modification of interferons from *Saccharomyces cerevisiae*. Curr. Genet. 12, 561–567.

26 Kalies, K-U., and Hartmann, E. (1996) Membrane topology of the 12 and the 25 kDa subunits of the mammalian signal peptidase complex. J. Biol. Chem. 271, 4325–4329.

30 Kyte, J. and Doolittle, R. F. (1982). A simple method for displaying the hydropathic character of a protein. J. Mol. Biol. 157, 105–132.

35 Newsome, A. L., McLean, J. W. and Lively, M. O. (1992) Molecular cloning of a cDNA encoding the glycoprotein of hen oviduct microsomal signal peptidase. Biochem. J. 282, 447–452.

37 Nunnari, J., Cox, T. D., and Walter, P. (1993) A mitochondrial protease with two catalytic subunits of nonoverlapping specificities. Science 262,1997–2004.

38 Pearson, W. R., and Lipman, D. J. (1988). Improved tools for biological sequence comparisons. Proc. Natl. Acad. Sci. USA 85, 2444–2448.

39 Perlman, K., and Halvorson, H. O. (1983). A putative signal peptidase recognition site and sequence in eukaryotic and prokaryotic signal peptides. J Mol. Biol. 167, 391–409.

40 Hitzeman, R. A., Chang, C. N., Matteucci, M., Perry, L. J., Kohr, W. J., Wulf, J. J., Swartz, J. R., Chen, C. Y., and Singh, A. (1986). Construction of expression vectors for secretion of human interferons by yeast. Methods Enzymol. 119, 424–433.

42 Sambrook, J., Fritsch, E. F. and Maniatis, T. (1989). Molecular Cloning: A laboratory Manual. 2nd edition. Cold Spring Harbor Laboratory Press.

45 Shelness, G. S. and Blobel, G. (1990). Two subunits of the canine signal peptidase complex are homologous to yeast SEC 11 protein. J. Biol. Chem. 265, 9512–9519.

46 Shelness, G. S., Kanwar, Y. S. and Blobel, G. (1988). cDNA-derived primary structure of the glycoprotein component of canine microsomal signal peptidase complex. J. Biol. Chem. 263, 17063–17070.

47 Shelness, G. S., Lin, L. and Nicchitta, C. V. (1993). Membrane topology and biogenesis of eukaryotic signal peptidase. J. Biol. Chem. 268, 5201–5208.

50 Simon, S. M. and Blobel, G. (1991). A protein-conducting channel in the endoplasmic reticulum. Cell 65, 371–380.

54 Sung, M., and Dalbey, R. E. (1992). Identification of potential active-site residues in the *Escherichia coli* leader peptidase. J. Biol. Chem. 267, 13154–13159.

61 YaDeau, J. T., Klein, C., and Blobel, G. (1991). Yeast signal peptidase contains a glycoprotein and the Sec11 gene product. Proc. Natl. Acad. Sci. USA 88, 517–521.

63 Zwizinski, C. and Wickner, W. (1980). Purification and characterization of leader (signal) peptidase from *Escherichia coli*. J. Biol. Chem. 255, 7973–7977.

64 McCabe, D. E., et al. (1988) Biotechnology 6, 923–926.

65 Yanisch-Perron, C., Vieire, J., and Messing, J. (1985) Gene 33, 103–199.

66 Berben, G., Dumont, J., Gilliquet, V., Bolle, P.-A., and Hilger, F. (1991) Yeast 7, 475–477.

67 Herman, P. K., and Emr, S. D. (1990) Mol. Cell Biol. 10, 6742–6754.

68 Sokorski, R. S. and Hieter, P. (1989) Genetics 122, 19–27.

69 Sherman, F., Fink, G. R., and Hicks, J. B. (1986) In: Methods in Yeast Genetics, pp.127–128, Cold Spring Harbor Laboratory, Cold Spring Harbor, N.Y.

70 Fang, H., Panzer, S., Mullins, C., Hartmann, E., and Green,, N. (1996) J. Biol. Chem. 271, 16460–16465

71. Christianson, T. W., Sikorski, R. S., Dante, M., Shero, J. H. and Hieter, P. (1992) Gene (Amst.) 110, 119–122.

72. Yanisch-Perron, C., Vieira, J. and Messing, J. (1985) Gene (Amst.) 33, 103–119.

73. Berben, G., Dumont, J., Gilliquest, V., Bolle, P.-A. and Hilger, F. (1991) Yeast 7, 475–477.

TABLE 1

Characterization of the subunits of the yeast signal peptidase complex

| Protein | M.W. (kDa) | Gene Disruption | Essential for Cell Growth | Proposed Function |
|---------|-----------|-----------------|---------------------------|-------------------|
| Sec11p  | 18        | Δsec11::HIS3    | Yes                       | catalytic subunit |
| Spc1p   | 11        | Δspc1::TRP1     | No                        | enzyme efficiency |
| Spc2p   | 20        | Δspc2::URA3     | No                        | complex stability |
| Spc3p   | 25        | Δspc3::LEU2     | Yes                       | catalytic subunit |

TABLE 2

Sequence comparisons between subunits of canine and yeast SPCs. The values are based on the number of amino acids in the yeast subunits. Homologies were derived by the method described in reference 38.

| Canine   | Yeast  | Identity | Similarity | Reference |
|----------|--------|----------|------------|-----------|
| SPC18    | Sec11p | 48%      | 75%        | (6,45)    |
| SPC21    | Sec11p | 45%      | 75%        | (6,20)    |
| SPC12    | Spc1p  | 24%      | 63%        | (13,26)   |
| SPC25    | Spc2p  | 20%      | 55%        | (19,33)   |
| SPC22/23 | Spc3p  | 24%      | 59%        | (17,46)   |

TABLE 3

Oligonucleotides used for PCR cloning of human SPC12:

```
Forward primer:  5'-GGGGATCCACGCCAGCCATGCTGGAGC-3'     (SEQ ID NO:5)
                     BamHI Reverse primer:  5'-GGGGAATTCAACCCAACTGGGCTAGAAA-3'    (SEQ ID NO:6)
                     EcoRI
```

Oligonucleotides used for PCR cloning of canine SPCIS:

```
Forward primer:  5'-GGGGATCCGGCCGCGCCATGCTGTCTC-3'     (SEQ ID NO:7)
                     BamHI Reverse primer:  5'-GGGGAATTCTTACTCACGATGGACCAG-3'     (SEQ ID NO:8)
                     EcoRI
```

Oligonucleotides used for PCR cloning of canine SPC21:

```
Forward primer:  5'-GGGGATCCAGCCCGCCATGGTGCGCGCGG-3'   (SEQ ID NO:9)
                     BamHI Reverse primer:  5'GGGGAATTCTCTTTTTAGGATTCACGT-3'      (SEQ ID NO:10)
                     EcoRI
```

Oligonucleotides used for PCR cioning of canine 5PC22/23:

```
Forward primer:  5'-GGGGATCCATGAACACGGTGCTGTCG         (SEQ ID NO:11)
                     BamHI Reverse primer:  5'-GGGATCGATTTAATAACTCTTCGTTA         (SEQ ID NO:12)
                     ClaI
```

Oligonucleotides used for PCR cloning of canine 5PC25:

```
Forward primer:  5'-GGGGATCCACAGACAAGATGGCGGCGGCGTCT-3' (SEQ ID NO:13)
```

TABLE 3-continued

BamHI
Reverse primer: 5'-GGGGAATTCTACTTTATCCATTTTAAGTTCTG-3'  (SEQ ID NO:14)
                    EcoRI

What is claimed is:

1. A yeast cell comprising a cDNA functionally encoding an exogenous eukaryotic protein homologue of a subunit of a yeast signal peptidase complex, wherein the eukaryotic protein homologue comprises a signal peptidase catalytic site.

2. The yeast cell of claim 1, wherein the eukaryotic protein homologue is a homologue of a Sec11p subunit of a yeast signal peptidase complex.

3. The yeast cell of claim 2, wherein the protein homologue is mammalian.

4. The yeast cell of claim 3, wherein the mammalian protein homologue is SPC18.

5. The yeast cell of claim 3, wherein the mammalian protein homologue is SPC21.

6. The yeast cell of claim 3, wherein the mammalian protein homologue is a truncated form of SPC21, wherein the negative element has been deleted from SPC21.

7. The yeast cell of claim 3, wherein the cDNA functionally encodes the mammalian protein homologues SPC18 and SPC21.

8. The yeast cell of claim 3, wherein the cDNA functionally encodes the mammalian protein homologues SPC18 and a truncated SPC21, wherein the negative element has been deleted from SPC21.

9. The yeast cell of claim 3, wherein the cDNA functionally encodes the mammalian protein homologues SPC18, SPC21 and a truncated SPC21, wherein the negative element has been deleted from SPC21.

10. The yeast cell of claim 1, wherein the yeast cell is a Saccharomyces cell.

11. The yeast cell of claim 1, wherein the yeast cell is a Schizosaccharomyces cell.

12. The yeast cell of claim 1, wherein the yeast cell is a Pichia cell.

13. The yeast cell of claim 1, wherein the yeast cell is a Hansenula cell.

14. The yeast cell of claim 1, wherein the yeast cell is a Kluyveromyces cell.

15. The yeast cell of claim 1, wherein the yeast cell is a Yarrowia cell.

16. The yeast cell of claim 1, wherein the eukaryotic protein homologue is a homologue of a Spc3p subunit of a yeast signal peptidase complex.

17. The yeast cell of claim 16, wherein the protein homologue is mammalian.

18. The yeast cell of claim 17, wherein the mammalian protein homologue is SPC22/23.

19. The yeast cell of claim 1, comprising two eukaryotic protein homologues, wherein the first eukaryotic protein homologue is a homologue of a Spc3p subunit of a yeast signal peptidase complex and the second eukaryotic protein homologue is a homologue of a Sec11p subunit of a yeast signal peptidase complex.

20. The yeast cell of claim 19, wherein the first eukaryotic protein homologue is mammalian and the second eukaryotic protein homologue is mammalian.

21. The yeast cell of claim 20, wherein the first eukaryotic protein homologue is SPC22/23 and the second eukaryotic protein homologue is a homologue selected from the group consisting of SPC 18, SPC21 and a truncated form of SPC21, wherein the negative element has been deleted from SPC21.

22. The yeast cell of claim 1, wherein the eukaryotic protein homologue is a homologue of a Spc1p subunit.

23. The yeast cell of claim 22, wherein the eukaryotic protein homologue is mammalian.

24. The yeast cell of claim 23, wherein the mammalian protein homologue is SPC12.

25. The yeast cell of claim 1, wherein the eukaryotic protein homologue is a homologue of a Spc2p subunit.

26. The yeast cell of claim 25, wherein the eukaryotic protein homologue is mammalian.

27. The yeast cell of claim 26, wherein the mammalian protein homologue is SPC25.

28. The yeast cell of claim 1, comprising two eukaryotic protein homologues, wherein the first eukaryotic protein homologue is a homologue of a Spc1p subunit of a yeast signal peptidase complex and the second eukaryotic protein homologue is a homologue of a Spc2p subunit of a yeast signal peptidase complex.

29. The yeast cell of claim 28, wherein the first eukaryotic protein homologue is mammalian and the second eukaryotic protein homologue is mammalian.

30. The yeast cell of claim 29, wherein the first eukaryotic protein homologue is SPC12 and the second eukaryotic protein homologue is SPC25.

31. The yeast cell of claim 1, wherein the cell lacks a functional Sec11p of a yeast signal peptidase complex.

32. The yeast cell of claim 1, wherein the cell lacks a functional Spc3p of a yeast signal peptidase complex.

33. The yeast cell of claim 1, wherein the cell lacks a functional Spc1p of a yeast signal peptidase complex.

34. The yeast cell of claim 1, wherein the cell lacks a functional Spc2p of a yeast signal peptidase complex.

35. A method of producing a protein heterologous to a yeast cell, comprising expressing, in the yeast cell of claim 1, a nucleic acid functionally encoding the heterologous protein under conditions which permit the expression of the nucleic acid as a precursor protein having a signal peptide and processing of the precursor protein to a signal peptide-cleaved form of the protein.

36. A method of obtaining increased production of a protein heterologous to a yeast cell, as compared to the level of heterologous protein produced in a yeast cell comprising only endogenous yeast signal peptidase complex subunits and with no exogenous eukaryotic protein homologue of a yeast signal peptidase complex in the cell, comprising introducing into the yeast cell of claim 1 a nucleic acid functionally encoding the heterologous protein under conditions which permit the expression of the nucleic acid as a precursor protein having a signal peptide and processing of the precursor protein to a signal peptide-cleaved form of a protein.

37. A method of producing a yeast cell comprising one or more exogenous eukaryotic protein homologues of a subunit of a yeast signal peptidase complex, comprising introducing into the yeast cell a cDNA functionally encoding one or more exogenous eucaryotic protein homologues of a subunit of a yeast signal peptidase complex under conditions which permit the expression of the cDNA as the protein homologue (s).

38. The method of claim 37, wherein the one or more exogenous eukaryotic protein homologues are selected from the group consisting of Sec11p, Spc1p, Spc2p and Spc3p.

39. The method of claim 37, wherein the cell lacks one or more functional subunits of the yeast signal peptidase complex.

40. The method of claim 39, wherein the one or more exogenous eukaryotic protein homologues are selected from the group consisting of Sec11p, Spc1p, Spc2p and Spc3p.

* * * * *